(12) United States Patent
Musso (10) Patent No.: US 12,055,504 B2
(45) Date of Patent: Aug. 6, 2024

(54) SYSTEMS AND METHODS FOR HIGH TEMPERATURE, HIGH PRESSURE ISOTHERMAL CALORIMETRY

(71) Applicant: Saudi Arabian Oil Company, Dhahran (SA)

(72) Inventor: Simone Musso, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 744 days.

(21) Appl. No.: 17/037,902

(22) Filed: Sep. 30, 2020

(65) Prior Publication Data

US 2021/0096092 A1 Apr. 1, 2021

Related U.S. Application Data

(60) Provisional application No. 62/907,940, filed on Sep. 30, 2019.

(51) Int. Cl.
| | |
|---|---|
| *G01K 17/00* | (2006.01) |
| *G01N 25/26* | (2006.01) |
| *G01N 25/48* | (2006.01) |

(52) U.S. Cl.
CPC ........... *G01N 25/486* (2013.01); *G01K 17/00* (2013.01); *G01N 25/26* (2013.01); *B01L 2300/168* (2013.01)

(58) Field of Classification Search
CPC .... G01N 25/486; G01N 25/26; G01N 33/383; G01K 17/00; B01L 2300/168
See application file for complete search history.

(56) References Cited

U.S. PATENT DOCUMENTS

| | | | |
|---|---|---|---|
| 3,789,662 A | 2/1974 | Zettler et al. | |
| 2003/0021329 A1* | 1/2003 | El-Gabry | G01N 25/18 374/43 |
| 2010/0255588 A1 | 10/2010 | Schenker | |
| 2011/0188534 A1* | 8/2011 | Nishimura | G01N 25/4866 374/33 |

(Continued)

FOREIGN PATENT DOCUMENTS

| | | | | |
|---|---|---|---|---|
| CA | 2864513 A1 * | 8/2013 | ........... | G01N 29/024 |
| CN | 204203147 U | 3/2015 | | |

(Continued)

OTHER PUBLICATIONS

17037902_2023-07-24_JP_2010276366_A_H.pdf,Dec. 9, 2010.*

(Continued)

*Primary Examiner* — Gail Kaplan Verbitsky
(74) *Attorney, Agent, or Firm* — Bracewell LLP; Constance G. Rhebergen; Keith R. Derrington (57) ABSTRACT

Methods and systems for high temperature, high pressure isothermal calorimetry are disclosed. The calorimetric system includes an ampoule having a body portion and a lid configured to completely seal the body portion. One or more solid reagents are disposed in the body portion of the ampoule, and a container is disposed within the body portion of the ampoule. The container separately stores one or more fluids for mixing with the one or more solid reagents. The lid is spring loaded and wound by a winding key for stirring the one or more solid reagents with the one or more fluids to form a homogenous mixture.

16 Claims, 6 Drawing Sheets

(56) References Cited

U.S. PATENT DOCUMENTS

| | | | | |
|---|---|---|---|---|
| 2015/0031142 | A1* | 1/2015 | Zhang | G01N 25/4826 422/51 |
| 2016/0041045 | A1* | 2/2016 | Ubelhor | G01N 25/20 374/33 |
| 2016/0223480 | A1 | 8/2016 | Jansson et al. | |
| 2019/0064009 | A1* | 2/2019 | Russell | G01N 25/4853 |

FOREIGN PATENT DOCUMENTS

| | | | | |
|---|---|---|---|---|
| CN | 109254032 | A | | 1/2019 |
| DE | 4406873 | A1 | * | 9/1994 ............ G01K 17/00 |
| EP | 1621828 | A1 | * | 2/2006 ............ F25B 17/08 |
| FR | 2840986 | A1 | * | 12/2003 ............ G01K 17/00 |
| FR | 3026828 | A1 | * | 4/2016 ............ F25B 17/00 |
| JP | S6165148 | A | * | 4/1986 |
| JP | 2009530083 | A | * | 8/2009 |
| JP | 2010276366 | A | * | 12/2010 |
| JP | 2010276366 | A | | 12/2010 |
| RU | 2371685 | C1 | | 10/2009 |
| SU | 466405 | A1 | | 4/1975 |
| SU | 893247 | A1 | * | 12/1981 |
| SU | 966592 | A1 | | 10/1982 |
| SU | 1016699 | A1 | | 5/1983 |
| SU | 1430765 | A2 | | 10/1988 |
| WO | WO-2005066607 | A1 | * | 7/2005 ........ B01F 15/00201 |
| WO | WO-2006100412 | A1 | * | 9/2006 ............ A47J 39/003 |
| WO | WO-2014172794 | A1 | * | 10/2014 ............ A61L 24/02 |

OTHER PUBLICATIONS

17037902_2023-12-04_WO_2014172794_A1_H.pdf,Oct. 30, 2014.*
17037902_2023-12-04_SU_893247_A1_H.pdf, Dec. 30, 1981.*
17037902_2023-11-30_FR_2840986_A1_H.pdf,Dec. 19, 2003.*
17037902_2023-12-04_DE_4406873_A1_H.pdf, Sep. 8, 1994*
17037902_2023-07-24_JP_2009530083_A_H.pdf,Aug. 27, 2009.*
17037902_2023-12-04_WO_2005066607_A1_H.pdf.Jul. 21, 2005.*
17037902_2023-12-04_CA_2864513_A1_H.pdf,Aug. 29, 2013.*
International Search Report and Written Opinion for International Application No. PCT/US2020/053634 (SA51176), report mail date Jan. 25, 2021; pp. 1-13.

* cited by examiner

SYSTEMS AND METHODS FOR HIGH TEMPERATURE, HIGH PRESSURE ISOTHERMAL CALORIMETRY

CROSS-REFERENCE TO RELATED APPLICATIONS

This application claims priority of U.S. Provisional Application No. 62/907,940, titled "SYSTEMS AND METHODS FOR HIGH TEMPERATURE, HIGH PRESSURE ISOTHERMAL CALORIMETRY," which was filed on Sep. 30, 2019, the entire contents of which are incorporated herein by reference.

TECHNICAL FIELD

Embodiments relate generally to calorimetry, and more particularly to systems and methods for high temperature and high pressure isothermal calorimetry.

BACKGROUND

Calorimetry is the science or act of measuring changes in state variables of a body for the purpose of deriving the heat transfer associated with changes of its state due, for example, to chemical reactions, physical changes, or phase transitions under specified constraints. Calorimetry is performed with a calorimeter.

Cement is a finely ground powder of burned limestone. It reacts readily with water (hydrates) to form a solid material, known as hardened cement paste. When cement is mixed together with rock aggregate, sand and filler materials, it forms concrete. Cement is one of the most important base materials in general use in the oil and gas industry. The optimization of concrete with respect to frost resistance, durability, chemical resistance etc. is of great importance. Cement hydration is a strongly exothermic reaction that takes place in a number of stages including rapid initial processes, induction (dormant) period, acceleration period, retardation period, and long-term reactions.

Isothermal calorimetry is a standard way to follow all stages of the hydration process. The measurements obtained from isothermal calorimetry is designed to demonstrate all stages of cement hydration. To study the first stage, it is necessary to mix water and cement inside the sample ampoule within the calorimeter. This is quite easy if there is a high water-cement ratio; however for lower, more realistic water content this is a more difficult experiment. For the long-term reactions of the last stage, a micro-calorimeter would have to be used to achieve the required increase in detectability. A widely used modern instrument is the differential scanning calorimeter, a device which allows thermal data to be obtained on small amounts of material. It involves heating the sample at a controlled rate and recording the heat flow either into or from the specimen.

The size restrictions imposed by using a standardized microtiter plate layout, such as described in the Standard ANSI/SBS 1-2004, places the heat producing sample vials in close proximity to each other and to the neighboring heat flow sensors. The insulation between individual samples of the microtiter plate will be through air. Infrared based heat radiation between samples poses the risk of inducing undesired cross sample heating and loss of sample accuracy.

SUMMARY

Accordingly, some have developed isothermal calorimeters for high pressure (for example, 1-15 bars) and high temperature (up to 150 degrees C.). Isothermal calorimetry measures heat developed or absorbed during a chemical reaction, occurring inside a sealed sample holder called "ampoule." The high temperature high pressure ampoule is made of steel to prevent it from bursting. However the ampoule has some limitations, in that it does not allow in-situ mixing and stirring of the reagents. When cement is mixed with water and exposed to high temperature, the kinetics of hydration is very quick. Hence it is best to mix the cement with water in-situ and start recording the reaction immediately. The best way to do this is to place the cement and the water in the steel ampoule, keeping them separated until the ampoule is placed in the calorimeter. Then, when the ampoule reaches the right temperature, one can mix cement and water together as quickly and as uniformly as possible.

Example embodiments relate to a modified high pressure high temperature ampoule for performing isothermal calorimetry. The ampoule includes a steel lid containing a mainspring manually wound up to store mechanical energy used to mix/stir, in-situ at high temperature and high pressure, a solid powder (e.g. cement) contained in the lower portion of the ampoule and water. The cement is placed in the bottom part of the ampoule (e.g. a steel container) whereas the water is placed inside a fragile glass container (the container is sealed at the bottom, but open at the top) on top of the cement.

Accordingly, one embodiment is a calorimetric system including an ampoule having a body portion and a lid configured to completely seal the body portion. One or more solid reagents is disposed in the body portion of the ampoule, and a container is disposed within the body portion of the ampoule. The container separately stores one or more fluids for mixing with the one or more solid reagents. The lid further includes a pressure valve configured to increase or decrease pressure within the ampoule, the pressure valve being coupled to one or more external pumps. The lid also includes a first sprocket wheel, and a first shaft coupled to the first sprocket wheel. The first sprocket wheel comprises a first spring configured to be wound by a first winding key. The lid further includes a second sprocket wheel at least partially engaged with the first sprocket wheel, and a second shaft coupled to the second sprocket wheel. The second sprocket wheel comprises a second spring configured to be wound by a second winding key. One or more blades are coupled to a bottom end of the second shaft, and the one or more blades are configured to break and container mix the one or more solid reagents with one or more fluids as the second spring unwinds.

Another example embodiment is a method for performing isothermal calorimetry. The method includes providing a predetermined amount of a solid reagent in an ampoule, the ampoule having a body portion and a lid configured to completely seal the body portion. The method also includes providing a predetermined volume of a fluid within a container, the container positioned within the body portion of the ampoule. The method further includes closing the lid over the body portion of the ampoule, thereby completely sealing the ampoule. The method also includes winding a sprocket wheel coupled to the lid, the sprocket wheel coupled to a shaft comprising one or more blades at a bottom end of the shaft, the one or more blades configured to break the container and mix the solid reagent with the fluid. The method further includes positioning the ampoule within a calorimeter, and mixing the solid reagent with the fluid to form a homogeneous mixture. The method may also include performing isothermal calorimetry in the calorimeter, and analyzing one or more characteristics of the solid reagent based on the calorimetry. The method may further include increasing or decreasing pressure within the ampoule via a pressure valve coupled to the lid of the ampoule, the pressure valve being coupled to one or more external pumps.

Another example embodiment is an ampoule including a body portion, a lid configured to completely seal the body portion, and a container disposed within the body portion of the ampoule, the container configured to store one or more fluids for mixing with one or more solid reagents. The lid may include a first sprocket wheel, and a first shaft coupled to the first sprocket wheel, the first sprocket wheel including a first spring configured to be wound by a first winding key. The lid may further include a second sprocket wheel at least partially engaged with the first sprocket wheel, and a second shaft coupled to the second sprocket wheel, the second sprocket wheel including a second spring configured to be wound by a second winding key. One or more blades may be coupled to a bottom end of the second shaft, the one or more blades configured to break the container and mix the one or more solid reagents with one or more fluids as the second spring unwinds.

BRIEF DESCRIPTION OF DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

For simplicity and clarity of illustration, the drawing figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of embodiments disclosed. Like reference numerals refer to like elements throughout the specification.

DETAILED DESCRIPTION

The methods and systems of the present disclosure will now be described more fully with reference to the accompanying drawings in which embodiments are shown. The methods and systems of the present disclosure may be in many different forms and should not be construed as limited to the illustrated embodiments set forth here; rather, these embodiments are provided so that this disclosure will be thorough and complete, and will fully convey its scope to those skilled in the art.

Figure 1:
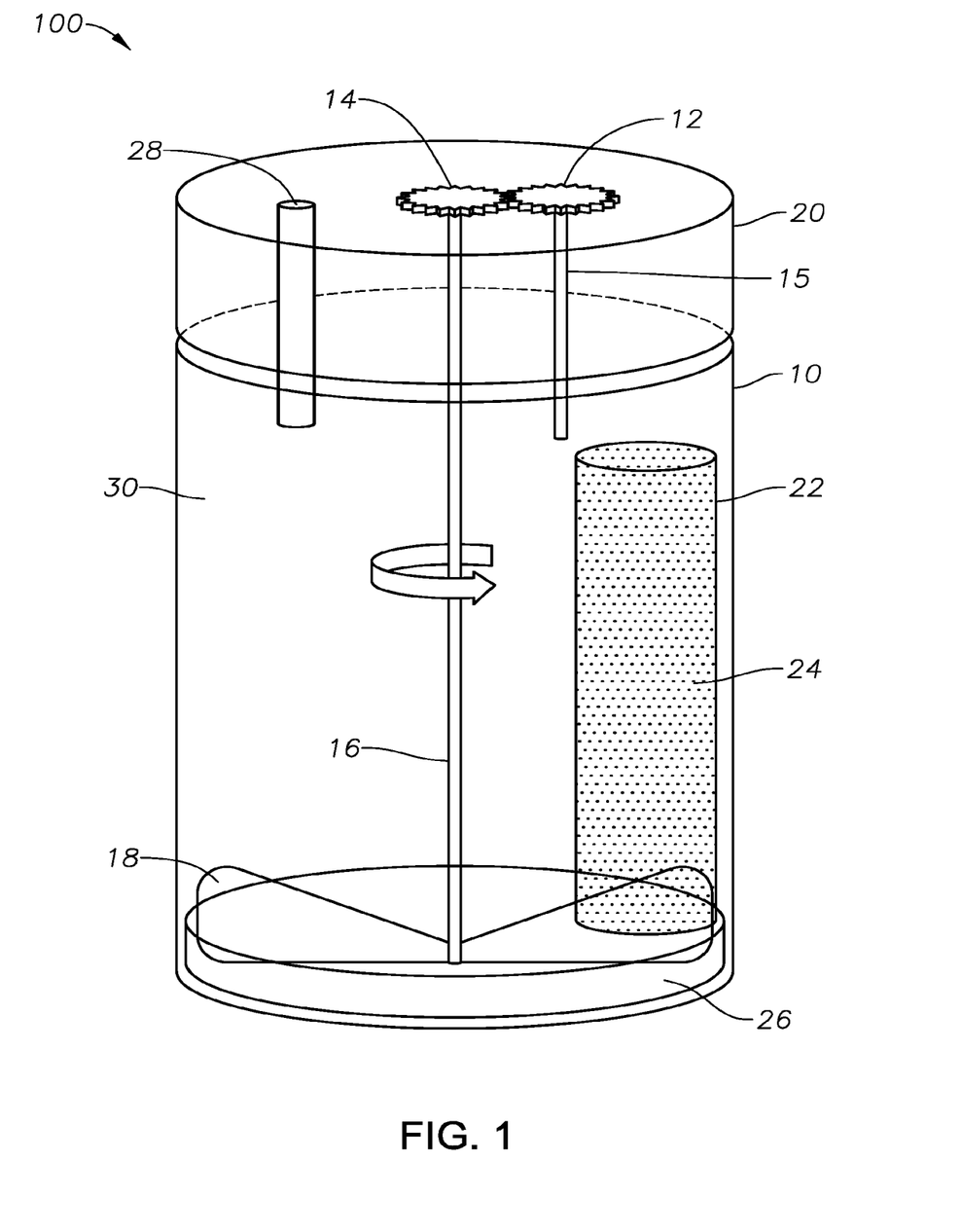
FIG. 1 is diagram illustrating an ampoule for performing isothermal calorimetry in accordance with one or more embodiments.

Turning now to the figures, FIG. 1 is diagram illustrating an ampoule 100 for performing isothermal calorimetry in accordance with one or more embodiments. Ampoule 100 may include a body portion or vial 10 and a lid 20 that is configured to completely seal the body portion or vial 10. Ampoule 100 may also include a container 22 that may be disposed within the body portion or vial 10 of the ampoule 100. The container 22 may be configured to store one or more fluids 24, such as water, for mixing with one or more solid reagents 26, for example cement. The container 22 may have a substantially cylindrical shape with an open top and a sealed bottom. Alternatively, the container 22 may have other shapes that may be apparent to one of ordinary skill in the art. The solid reagent 26 may be provided at the bottom of the body portion or vial 10. The lid 20 may include a first sprocket wheel 12 and a first shaft 15 that may be coupled to the first sprocket wheel 12.

The lid 20 may further include a second sprocket wheel 14 that may be activated by the first sprocket wheel 12. A second shaft 16 may be coupled to the second sprocket wheel 14. The second sprocket wheel 14 may also be spring loaded and may be wound using a second winding key, which may be the same as the first winding key or different from the first winding key. One or more blades 18 may be coupled to a bottom end of the second shaft 16. The one or more blades 18 are designed and configured in a way to break the container and efficiently mix the one or more solid reagents 26 with one or more fluids 24 as the second spring unwinds. The extent of winding of the first sprocket wheel 12 and/or second sprocket wheel 14 and the unwinding time may be predetermined based on the composition of the solid reagent and/or the fluid.

As illustrated in FIG. 1, the lid 20 includes several parts. In one embodiment, a pressure valve 28 that allows to pressurize the ampoule 100 when it is closed and sealed may be provided. The pressure valve 28 is configured to increase or decrease pressure within the ampoule 100 by coupling to one or more external pumps (not shown).

Figure 2:
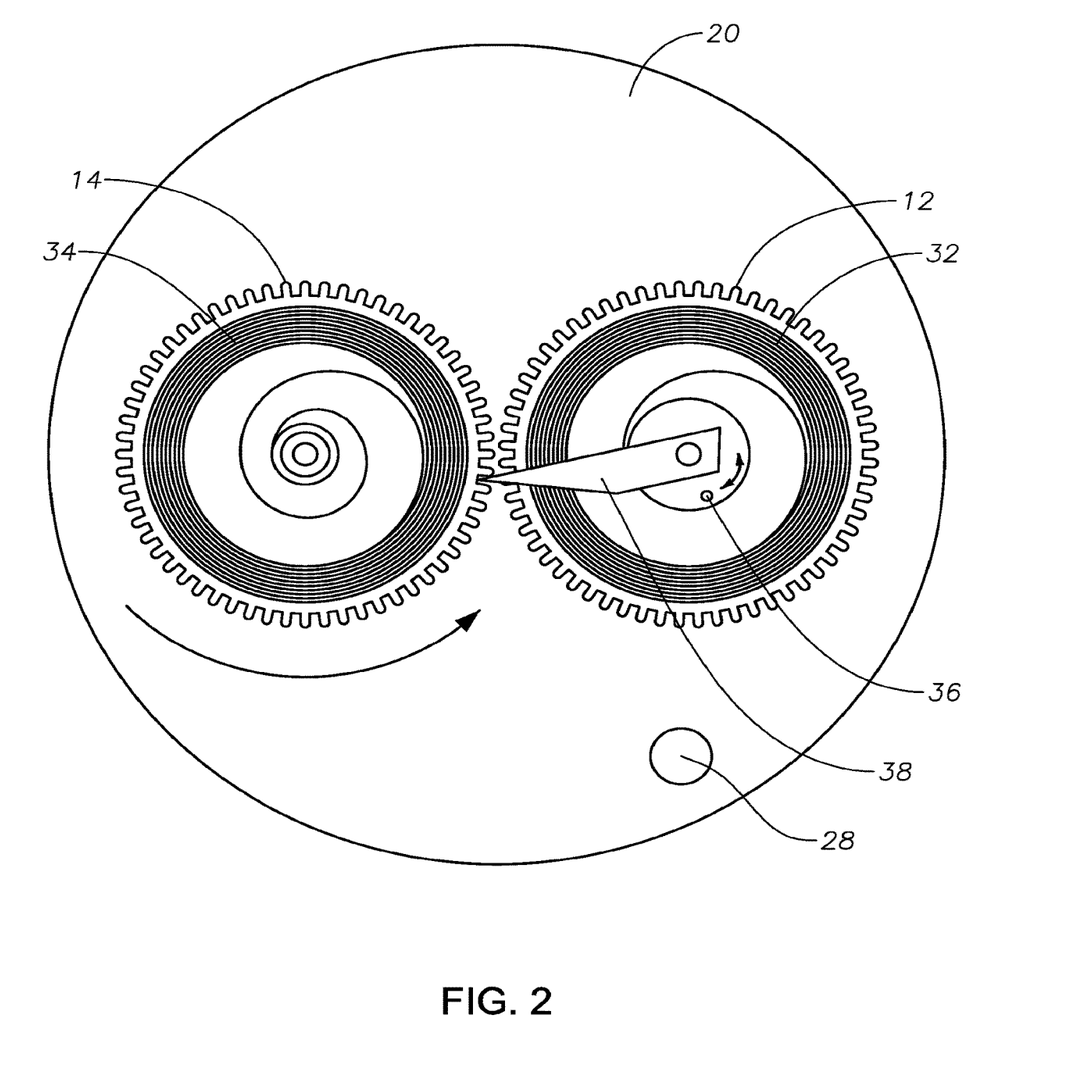
FIG. 2 illustrates a bottom perspective view of a lid configured to close an ampoule for performing isothermal calorimetry in accordance with one or more embodiments.

FIG. 2 illustrates a bottom perspective view of the lid 20. As illustrated in this figure, the first sprocket wheel 12 includes a first mechanical spring 32 that can be wound, using a winding key, to store mechanical energy. Spring 32 serves as a mechanical timer, which is released over approximately a minute (depending on the design of spring 32). When the spring 32 unwinds completely and the energy within the spring is depleted, pin 36 triggers or unlocks a ratchet 38 that releases second sprocket wheel 14 that can then activate the stirring blades 18.

The second sprocket wheel 14 also includes a mechanical spring 34. Spring 34 is used to accumulate and store energy, by winding the coiled spring 34 using a winding key, and the mechanical energy stored within this spring 34 can be used to stir or mix the reagent 26 with the fluid when the pin 36 unlocks the ratchet 38 that releases second sprocket wheel 14. The mixer shaft 16 is used both to wind up spring 34 and to connect the mainspring 34 to the mixer rod 16 and blades 18 used for the mixing the reagent 26 with the fluid 24. When the ratchet releases the second sprocket wheel, the mechanical energy within the second coil spring is released and the shaft including the one or more blades at a bottom end of the shaft is rotated. The rotation of the blades causes the solid reagent to mix with the fluid to form a homogeneous mixture.

Alternatively, instead of using an analog mechanical timer as described in FIGS. 1 and 2, a digital electronic timer may be used to rotate a shaft using, for example, an electric motor that can be accommodated within the body of the lid 20. The electric motor can be powered by a battery or any other power storage device known to one of skill in the art.

The body portion or vial 10 may have a substantially cylindrical shape and the lid 20 may have a corresponding shape for completely sealing the body portion or vial 10. The body portion or vial 10 may be made of glass or stainless steel, or any material that may withstand high pressure and high temperature. Similarly, the lid 20 and the container 22 may also be made of glass or stainless steel, or any material that may withstand high pressure and high temperature.

Figure 3:
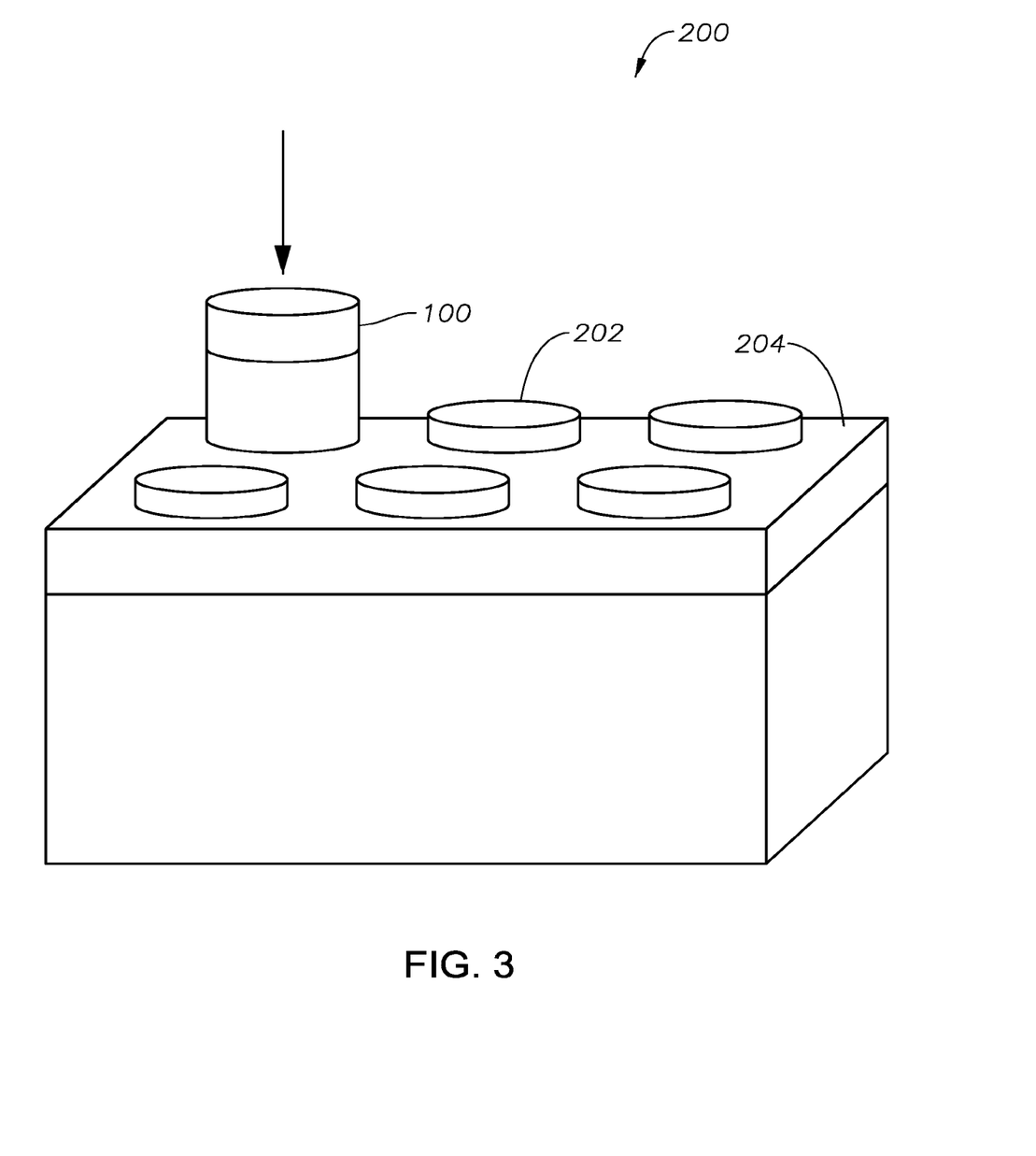
FIG. 3 is diagram illustrating a calorimeter including an ampoule for performing isothermal calorimetry in accordance with one or more embodiments.

FIG. 3 is diagram illustrating a calorimeter 200 including a plurality of ampoules 100 for performing isothermal calorimetry in accordance with one or more embodiments. The calorimeter may include a calorimeter block 204 where the plurality of ampoules 200 may be positioned. The calorimeter 200 may be suitable for isothermal calorimeter with heat flow sensitivity in the microwatt range and a good baseline drift performance. The calorimeter may have an operating temperature range of about 5 degrees C. to about 150 degrees C. It may include a circulating air thermostat with temperature stability at ±0.02 degrees C. The calorimeter 200 may have channel configuration 202 that may be an 8-channel or 3-channel calorimeter configuration (shown). The calorimeter 200 may connected up to 8 external probes including I/O voltage cards. The calorimetric channels are of the twin type, consisting of a sample and a reference chamber. The 8 channel calorimeter can accommodate ampoules with a 20 mL volume. The 3 channel calorimeter can accommodate ampoules with a 125 mL volume. Air flows upward through a temperature regulating heat sink and then through inner chamber directly around the calorimeter block. It then flows downward through the outer space surrounding the inner chamber, in effect isolating the inner chamber from external thermal noise and ensuring greater long-term stability and lower thermal noise.

Figure 4:
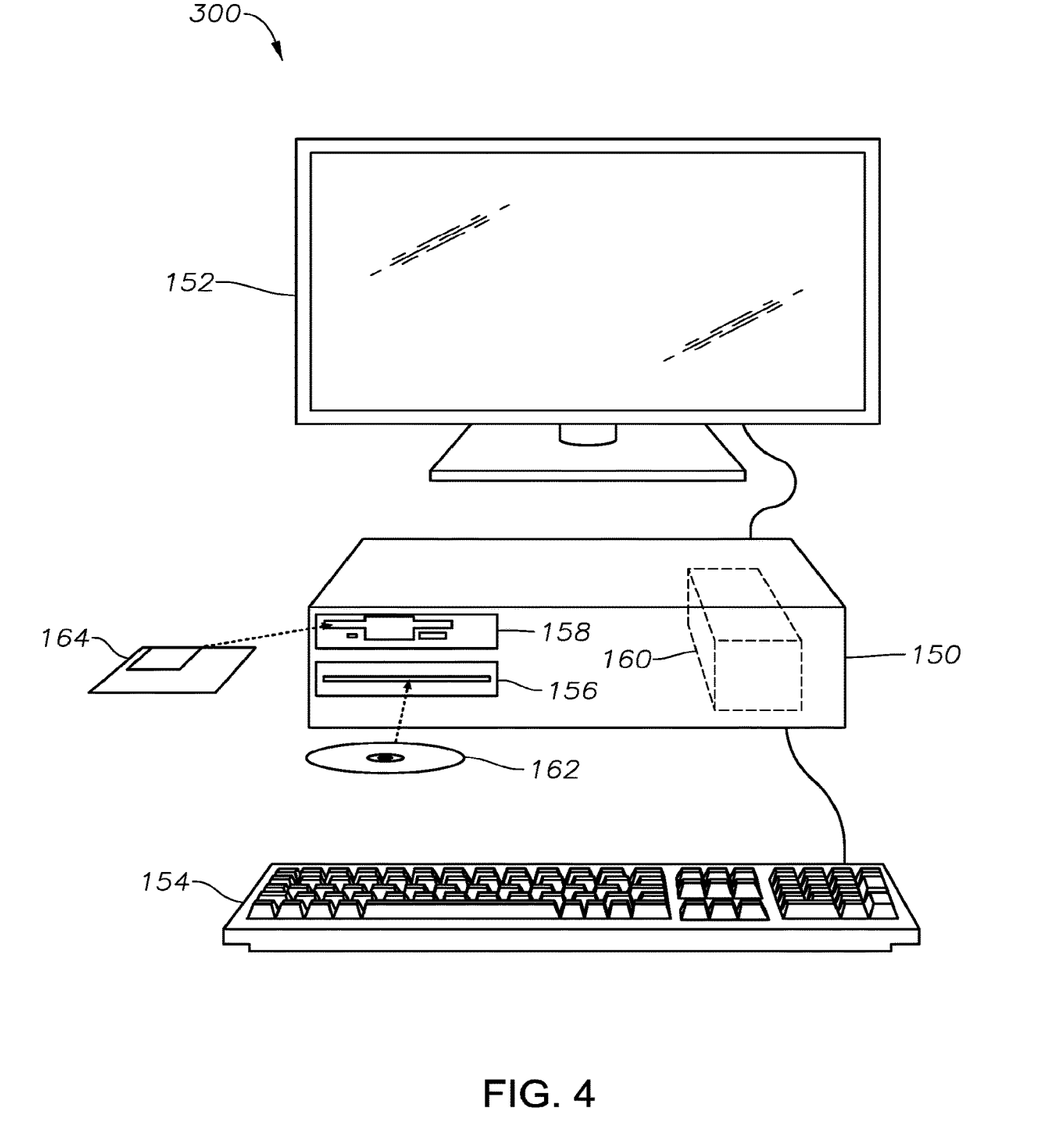
FIG. 4 is diagram illustrating a computer system for performing isothermal calorimetry in accordance with one or more embodiments.

FIG. 4 is diagram illustrating a computer system 300 for performing isothermal calorimetry in accordance with one or more embodiments. System 300 may be coupled to the calorimeter 200 to receive data from the isothermal calorimetry. The data may be used to analyze and determine one or more characteristics of the cement. Referring to FIG. 4, the foregoing process of receiving and analyzing data from the calorimeter can be embodied in computer-readable code. The code can be stored on, for example, a non-transitory computer readable medium, such as a floppy disk 164, CD-ROM 162, which may be read by disk drives 158, 156, or a magnetic (or other type) hard drive 160 forming part of a special purpose programmable computer. The computer may include one or more processors, such as a central processing unit 150, a user input device such as a keyboard 154, and a user display 152 such as a flat panel liquid crystal display (LCD) or light emitting diode (LED) display. According to this embodiment, the non-transitory computer-readable medium 160, 162, 164 may have, for example, computer executable instructions that cause the computer to perform the operations of receiving data from the isothermal calorimetry, and analyzing the data to determine one or more characteristics of the solid reagent.

Figure 5:
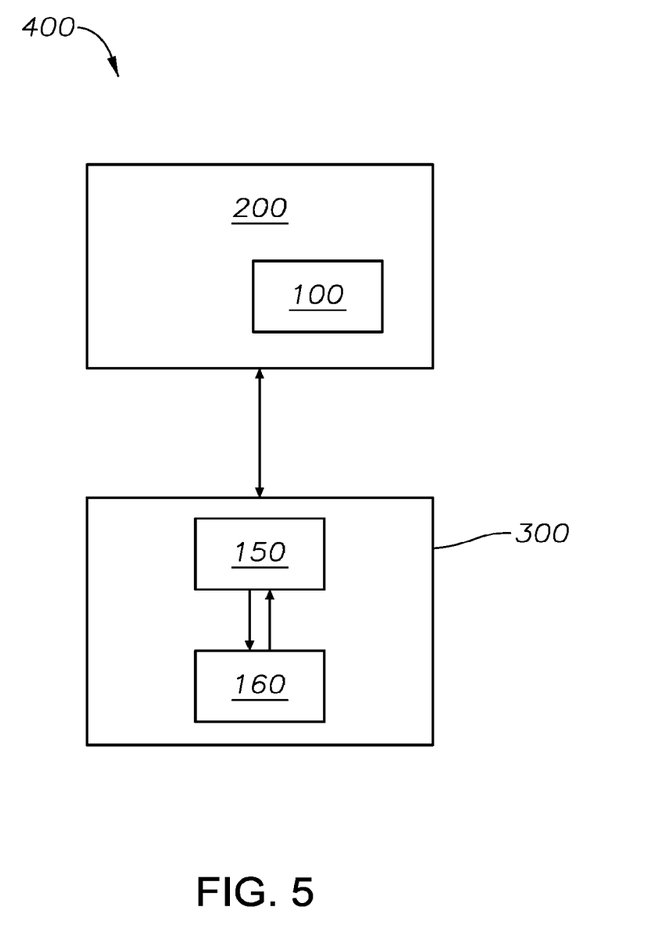
FIG. 5 is diagram illustrating a calorimetric system including a calorimeter, an ampoule, and a computer system for performing isothermal calorimetry in accordance with one or more embodiments.

FIG. 5 is diagram illustrating a calorimetric system 400 including a calorimeter 200, an ampoule 100, and a computer system 300 for performing isothermal calorimetry in accordance with one or more embodiments. The system 300 may also include a computer having one or more processors 150 and a non-transitory computer readable medium 160, which may include computer executable instructions that when executed by the one or more processors 150, cause the computer 300 to receive data from the isothermal calorimetry, and analyze the data to determine one or more characteristics of the solid reagent.

Figure 6:
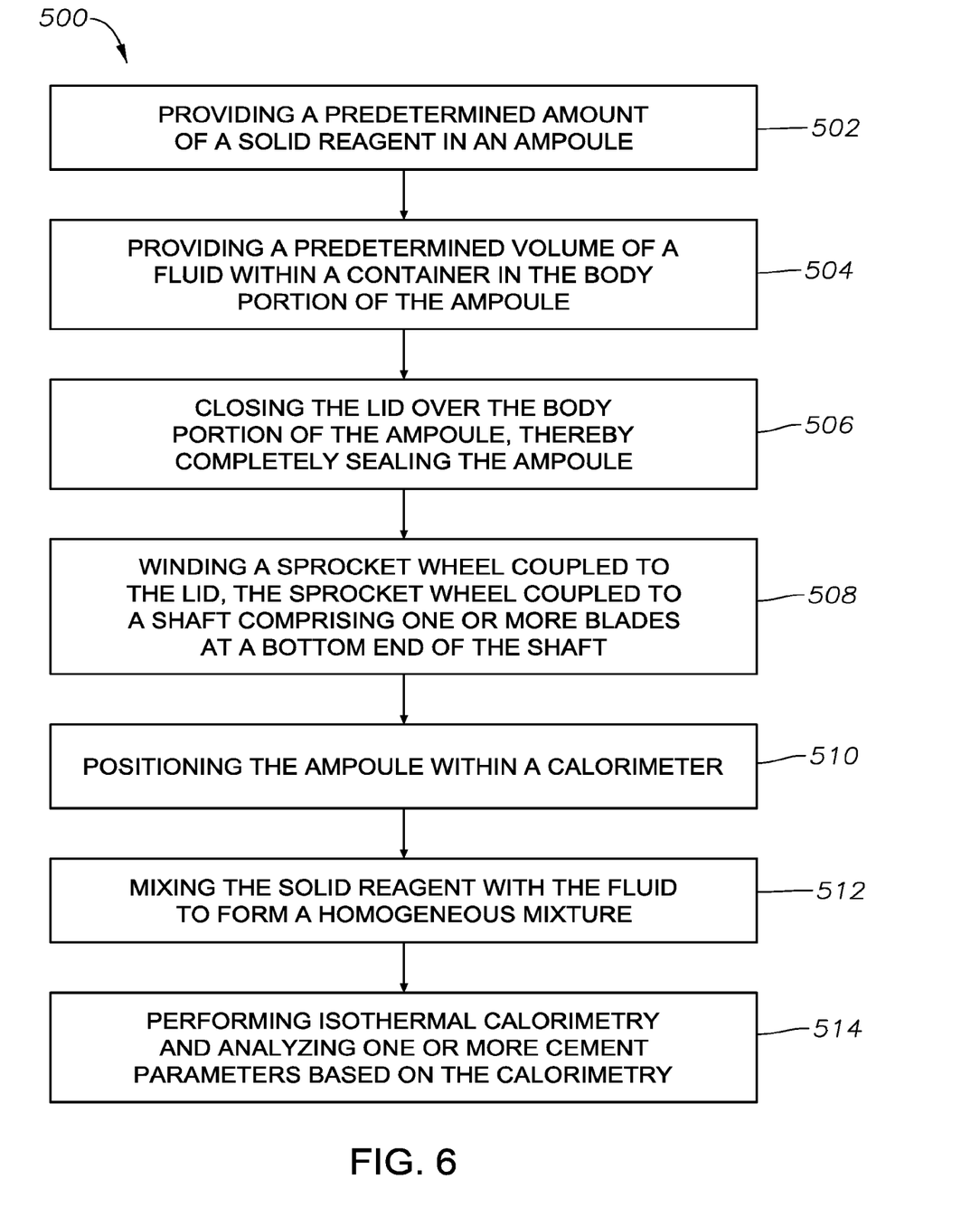
FIG. 6 is a flow chart illustrating example steps in a method for performing isothermal calorimetry in accordance with one or more embodiments.

FIG. 6 is a flow chart illustrating example steps in a method 500 for performing isothermal calorimetry in accordance with one or more embodiments. The method 500 includes, at step 502, providing a predetermined amount of a solid reagent in an ampoule. The ampoule may have a body portion or vial, and a lid configured to completely seal the body portion. The method also includes, at step 504, providing a predetermined volume of a fluid within a container. The container may be positioned within the body portion or vial of the ampoule. The method further includes, at step 506, closing the lid over the body portion or vial of the ampoule, thereby completely sealing the ampoule. The method also includes, at step 508, winding a sprocket wheel coupled to the lid. The sprocket wheel may include a coil spring that may be wound by winding key to store mechanical energy. The method further includes, at step 510, positioning the ampoule within a calorimeter. When the spring unwinds completely and the stored energy within the coil spring is depleted, a ratchet locking a second sprocket wheel may be unlocked or activated. The second sprocket wheel may also include a coil spring that may be wound using a winding key. The second sprocket wheel may be coupled to a shaft including one or more blades at a bottom end of the shaft. When the ratchet releases the second sprocket wheel, the mechanical energy within the second coil spring is released and the shaft including one or more blades at a bottom end of the shaft is rotated. The rotation of the blades causes the solid reagent to mix with the fluid to form a homogeneous mixture at step 512. The one or more blades are configured to break the container and mix the solid reagent with the fluid as the spring unwinds. The method may also include, at step 514, performing isothermal calorimetry in the calorimeter, and analyzing one or more characteristics of the solid reagent based on the calorimetry results. The method may further include increasing or decreasing pressure within the ampoule via a pressure valve coupled to the lid of the ampoule. The pressure valve may be coupled to one or more external pumps, which may form part of the system.

In some embodiments, the vial material includes, but is not limited to, titanium alloys. The vial may be partially or fully coated with an infrared reflective coating including, but is not limited to, titanium nitride. The infrared reflective coating may be include Gold (Au) or ceramic compounds including, but not limited to, titanium nitride. The infrared reflective coating may have a coating thickness between 0.5 µm and 4 µm.

In some embodiments, the lid material is of low mass, and the lid may also be at least partially coated with an infrared reflective coating on the outside of the lid. The lid material may include, but is not limited to, titanium alloys, and the infrared reflective coating includes, but is not limited to, titanium nitride. The infrared reflective coating may be include Gold (Au) or ceramic compounds including, but not limited to, titanium nitride. The infrared reflective coating may have a coating thickness between 0.5 µm and 4 µm.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims. Headings used here are for organizational purposes only and are not meant to be used to limit the scope of the description.

It will be appreciated that the processes and methods described here are example embodiments of processes and methods that may be employed in accordance with the techniques described here. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

The Specification, which includes the Summary, Brief Description of the Drawings and the Detailed Description, and the appended Claims refer to particular features (including process or method steps) of the disclosure. Those of skill in the art understand that the disclosure includes all possible combinations and uses of particular features described in the Specification. Those of skill in the art understand that the disclosure is not limited to or by the description of embodiments given in the Specification.

Those of skill in the art also understand that the terminology used for describing particular embodiments does not limit the scope or breadth of the disclosure. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this disclosure belongs unless defined otherwise.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

The systems and methods described here, therefore, are well adapted to carry out the objects and attain the ends and advantages mentioned, as well as others inherent there. While example embodiments of the system and method have been given for purposes of disclosure, numerous changes exist in the details of procedures for accomplishing the desired results. These and other similar modifications may readily suggest themselves to those skilled in the art, and are intended to be encompassed within the spirit of the system and method disclosed here and the scope of the appended claims.

The invention claimed is:

1. A calorimetric system comprising:
an ampoule having a body portion and a lid configured to completely seal the body portion, the lid comprising,
the first sprocket wheel,
a first coil spring coupled to the first sprocket wheel, and
a first shaft coupled to the first sprocket wheel;
one or more solid reagents disposed in the body portion of the ampoule;
a pressure valve coupled to one or more external pumps and configured to increase or decrease pressure within the ampoule; and
a container disposed within the body portion of the ampoule, the container separately storing one or more fluids for mixing with the one or more solid reagents.

2. The calorimetric system according to claim 1, wherein the first spring is configured to be wound by a first winding key.

3. The calorimetric system according to claim 2, wherein the lid further comprises:
a second sprocket wheel;

a second coil spring coupled to the second sprocket wheel; and a second shaft coupled to the second sprocket wheel, wherein the second spring is configured to be wound by a second winding key.

4. The calorimetric system according to claim 3, wherein the lid further comprises:

one or more blades coupled to a bottom end of the second shaft, wherein the one or more blades are configured to mix the one or more solid reagents with one or more fluids as the second spring unwinds.

5. The calorimetric system according to claim 3, wherein the second sprocket wheel is locked from rotating using a ratchet coupled to the first sprocket wheel, and wherein the ratchet is released by a pin associated with the first sprocket wheel.

6. The calorimetric system according to claim 1, wherein the body portion has a substantially cylindrical shape and the lid has a corresponding shape for completely sealing the body portion.

7. The calorimetric system according to claim 1, wherein the body portion comprises glass or stainless steel.

8. The calorimetric system according to claim 1, wherein the lid comprises glass or stainless steel.

9. The calorimetric system according to claim 1, wherein the container comprises glass or stainless steel.

10. A method for performing isothermal calorimetry, the method comprising:

providing a predetermined amount of a solid reagent in an ampoule, the ampoule having a body portion and a lid configured to completely seal the body portion;

providing a predetermined volume of a fluid and a reagent within a container, the container positioned within the body portion of the ampoule;

closing the lid over the body portion of the ampoule;

placing the ampoule within a calorimeter;

winding a sprocket wheel coupled to the lid, the sprocket wheel coupled to a shaft comprising one or more blades at a bottom end of the shaft, the one or more blades configured to mix the solid reagent with the fluid; and measuring a heat flow within the ampoule.

11. The method according to claim 10, wherein the reagent is solid reagent, the method further comprising forming a homogeneous mixture with the reagent and the liquid.

12. The method according to claim 10, further comprising:

analyzing one or more characteristics of the solid reagent based on the measured change.

13. The method according to claim 10, further comprising:

changing pressure within the ampoule via a pressure valve coupled to the lid of the ampoule, wherein the pressure valve is coupled to one or more external pumps.

14. A method for performing isothermal calorimetry comprising:

obtaining an ampoule having a body portion, a container in the body portion, a lid configured to completely seal the body portion;

disposing a reagent in the body portion;

disposing a fluid in the container;

placing the ampoule within a calorimeter;

mixing the reagent with the fluid;

measuring a heat flow within the ampoule; and delaying the step of mixing the reagent with the fluid for a period of time after the step of placing the ampoule within the calorimeter.

15. The method of claim 14, wherein the step of delaying comprises using a mechanical timer comprising a first spring and wherein the step of mixing comprises using a blade that is driven by a second spring.

16. The method of claim 14, further comprising pressurizing the ampoule through a pressure valve provided in the lid.

* * * * *

UNITED STATES PATENT AND TRADEMARK OFFICE
CERTIFICATE OF CORRECTION

PATENT NO. : 12,055,504 B2
APPLICATION NO. : 17/037902
DATED : August 6, 2024
INVENTOR(S) : Simone Musso

Page 1 of 1

It is certified that error appears in the above-identified patent and that said Letters Patent is hereby corrected as shown below:

In the Claims

Column 8, Claim 1, Line 50:
""the first sprocket wheel,""
Should be changed to:
--a first sprocket wheel,--

Signed and Sealed this
Tenth Day of September, 2024

Katherine Kelly Vidal
*Director of the United States Patent and Trademark Office*